United States Patent [19]

Toot, Jr. et al.

[11] Patent Number: 5,414,022
[45] Date of Patent: * May 9, 1995

[54] PROCESS OF RECOVERING COMPONENTS FROM POLYESTER RESINS

[75] Inventors: Walter E. Toot, Jr.; Bruce R. Debruin, both of Rochester, N.Y.

[73] Assignee: Eastman Kodak Company, Rochester, N.Y.

[*] Notice: The portion of the term of this patent subsequent to Mar. 29, 2011 has been disclaimed.

[21] Appl. No.: 209,150

[22] Filed: Mar. 10, 1994

[51] Int. Cl.$^6$ .............................................. C08J 11/04
[52] U.S. Cl. ..................................... 521/48; 521/48.5; 528/496; 528/503; 560/78
[58] Field of Search .................. 521/48, 48.5; 528/496, 528/503; 560/78

[56] References Cited

U.S. PATENT DOCUMENTS

| | | | |
|---|---|---|---|
| 3,037,050 | 5/1962 | Helsenberg et al. | 560/96 |
| 3,321,510 | 5/1967 | Lotz et al. | 560/96 |
| 3,776,945 | 12/1973 | Ligorati et al. | 260/475 |
| 3,884,850 | 5/1975 | Ostrowski | 260/2.3 |
| 3,904,868 | 9/1975 | Currie et al. | 260/475 X |
| 4,163,860 | 8/1979 | Delattre et al. | 560/96 |
| 4,578,502 | 3/1986 | Cudmore | 528/308.4 |
| 4,620,032 | 10/1986 | Doerr | 562/483 |
| 4,929,749 | 5/1990 | Gupta et al. | 560/79 |
| 5,051,528 | 9/1991 | Naujokas et al. | 560/78 |
| 5,095,145 | 3/1992 | Rosen | 562/483 |
| 5,298,530 | 3/1994 | Gamble et al. | 521/48.5 |

FOREIGN PATENT DOCUMENTS 484963 11/1991 European Pat. Off. ..... C07C 69/82

Primary Examiner—Paul R. Michl
Assistant Examiner—Olga Asinovsky
Attorney, Agent, or Firm—Joshua G. Levitt

[57] ABSTRACT

There is described a process and optimal conditions for depolymerizing polyester into its components and separating the components using apparatus comprising:
  a dissolver for receiving polyester,
  a reactor for depolymerizing polyester into components, and
  a rectifier for separating polyester components; the process comprising the steps of:
  a) adding polyester to the dissolver and combining it with melt from the reactor and liquid from the rectifier to reduce the chain length of the polyester,
  b) transferring reduced chain length polyester from the dissolver to the reactor,
  c) passing super-heated methanol through the reactor to depolymerize polyester into its constituent monomers;
  d) transferring depolymerization products from the reactor to the rectifier; and
  e) separating the depolymerization products in the rectifier into a vapor phase containing component monomers and a liquid phase containing higher molecular weight materials.

10 Claims, 1 Drawing Sheet

PROCESS OF RECOVERING COMPONENTS FROM POLYESTER RESINS

FIELD OF THE INVENTION

This invention relates to a process for recovery of monomer components from condensation-type polyester resins such as polyethylene terephthalate and polyethylene naphthalate.

BACKGROUND OF THE INVENTION

Polyester resins have found widespread use in varied applications. Polyester resins, such as polyethylene terephthalate and polyethylene naphthalate, are used in films, including photographic film and magnetic tape, in fibers, and in food containers such as bottles and beverage containers. Various methods have been disclosed for the depolymerization of such resins into their component monomers, such as ethylene glycol, terephthalic acid, naphthalic acid, or derivatives thereof, so that they could be reused.

U.S. Pat. No. 5,051,528 describes a process of recovering ethylene glycol and dimethyl terephthalate from polyethylene terephthalate scrap resins by dissolving the polyester resin in oligomers of the same monomers as present in the polyester, passing super-heated methanol through the solution and recovering ethylene glycol and dimethyl terephthalate.

Commonly assigned, copending U.S. patent application Ser. No. 07/981,688 describes an improvement in the process of the '528 patent in which the scrap resin is combined with reactor melt in a dissolver, before the dissolver melt is transferred to a reactor for contact with super-heated methanol. In one embodiment, the polyester is combined in the dissolver with, in addition to reactor melt, other components exiting the reactor.

Other art describing recovery of monomer from polyester resins is noted in the above patent and application.

SUMMARY OF THE INVENTION

The present invention improves upon the process of the '528 patent and the '688 application by providing optimal ways of controlling the viscosity of the melt in the dissolver and results in optimal residence times and heat transfer characteristics. This permits efficient recovery of monomer from polyester resin.

Thus, in one embodiment the present invention provides a process for depolymerizing polyester into its components and separating the components using apparatus comprising:
a dissolver for receiving polyester,
a reactor for depolymerizing polyester into components, and
a rectifier for separating polyester components; the process comprising the steps of:
a) adding polyester to the dissolver and combining it with melt from the reactor and liquid from the rectifier to reduce the chain length of the polyester,
b) transferring reduced chain length polyester from the dissolver to the reactor,
c) passing super-heated methanol through the reactor to depolymerize polyester into its constituent monomers;
d) transferring depolymerization products from the reactor to the rectifier; and
e) separating the depolymerization products in the rectifier into a vapor phase containing component monomers and a liquid phase containing higher molecular weight materials;
wherein
  i) the dissolver is operated at a temperature of 180° to 270° C. and a pressure of 80 to 150 kilopascals absolute (kPaa),
  ii) the reactor is operated at a temperature in the range of 180° to 305° C., and a pressure in the range of 101 to 800 kPaa,
  iii) the relative proportions, on a weight basis, of melt from the reactor and liquid from the rectifier fed to the dissolver is in the range of 0 to 1 parts liquid per part melt, and
  iv) the relative proportions on a weight basis of reactor melt plus rectifier liquid and polyester fed to the dissolver is in the range of 0 to 10 parts reactor melt plus rectifier liquid per part polyester,
so that the viscosity of the polyester exiting the dissolver is maintained in the range of 0.001 to 0.2 Pascal seconds (Pa.s).

In a preferred embodiment, the dissolver is operated at a temperature in the range of 215° to 260° C. and a pressure in the range of 90 to 130 kPaa,
the reactor is operated at a temperature in the range of 220° to 285° C., and a pressure in the range of 200 to 620 kPaa,
the relative proportions, on a weight basis, of melt from the reactor and liquid from the rectifier fed to the dissolver is in the range of 0 to 0.5 parts liquid per part melt,
the relative proportions on a weight basis of reactor melt plus rectifier liquid and polyester fed to the dissolver is in the range of 0.2 to 1 parts reactor melt plus rectifier liquid per part polyester, and
the viscosity of the polyester exiting the dissolver is maintained in the range of 0.002 to 0.1 Pa.s In a particularly preferred embodiment, the dissolver is operated at a temperature in the range of 240° to 255° C. and a pressure in the range of 95 to 105 kPaa,
the reactor is operated at a temperature in the range of 250° to 280° C., and a pressure in the range of 240 to 410 kPaa,
the relative proportions, on a weight basis, of melt from the reactor and liquid from the rectifier fed to the dissolver is in the range of 0 to 0.25 parts liquid per part melt,
the relative proportions on a weight basis of reactor melt plus rectifier liquid and polyester fed to the dissolver is in the range of 0.2 to 0.4 parts reactor melt plus rectifier liquid per part polyester, and
the viscosity of the polyester exiting the dissolver is maintained in the range of 0.01 to 0.04 Pa.s.

When operated in this way, the residence time of the polyester in the dissolver required to completely liquify the polyester is in the range of 10 to 90 minutes. Preferably it is in the range of 10 to 70 minutes and most preferably it is in the range of 30 to 65 minutes. Average residence time in the dissolver is equal to the volume of material in the dissolver divided by the rate at which material exits the dissolver.

We have found that for optimal recovery of materials, a scrubber should be connected to the dissolver to remove terephthalate contained in the gas that exits the dissolver. This use of the scrubber leads results in an advantage accruing from using both rectifier liquid and reactor melt to control the viscosity of the dissolver melt. Rectifier liquid is more effective than reactor melt for producing the desired viscosity and other desired parameters like residence time and heat transfer characteristics. However, rectifier liquid also produces more gases that need to be sent to the scrubber. By controlling the ratio of rectifier liquid to reactor melt, one obtains the optimum benefits for the dissolver, while minimizing the impact on the scrubber. One must maintain a balance between the condition where not enough rectifier liquid is used that the viscosity can not be maintained at the desired level and the condition where so much rectifier liquid is used that the scrubber is overloaded with gas. While in the ideal system, no rectifier liquid would be used, in a practical system, some rectifier liquid is needed to maintain the viscosity and the desired level. This typically is achieved when the ratio of rectifier liquid to reactor melt is in the range of 0.01 to 0.5 parts by weight, and more frequently in the range of 0.05 to 0.25 parts by weight.

In the following description of this invention polyethylene terephthalate will be used to illustrate the practice of the invention. It will be understood that the invention also is applicable to other condensation polyesters, such as polyethylene naphthalate.

DESCRIPTION OF THE PREFERRED EMBODIMENTS

Figure 1:
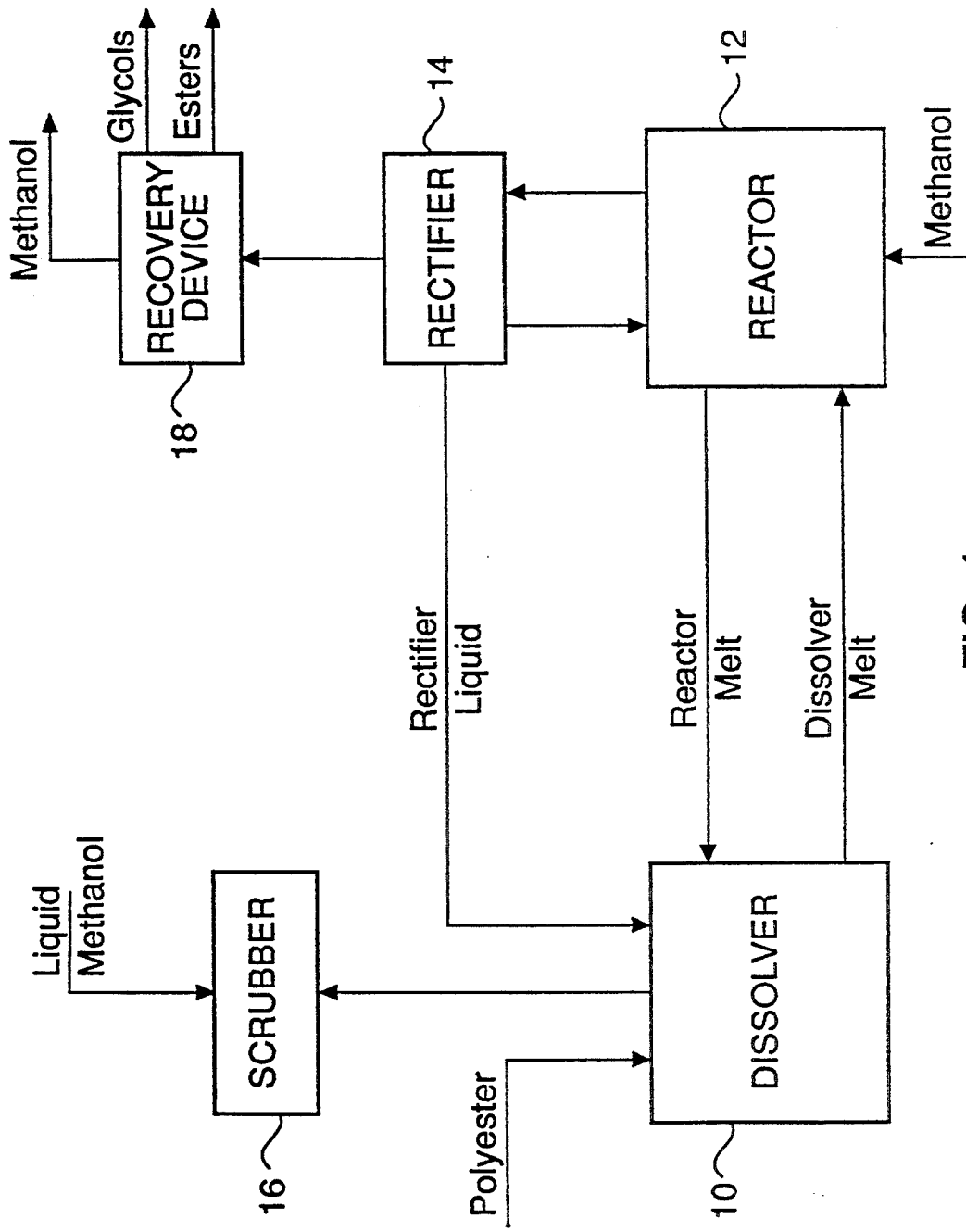
FIG. 1 is a schematic flow diagram illustrating the process of this invention.

FIG. 1 schematically illustrates apparatus to carry out the process of the invention. It comprises a dissolver 10, a reactor 12 and a rectifier 14, connected by pipes, pumps and valves to transfer the materials in accordance with the process of the invention. Also shown is a scrubber 16, for recovering gases from the dissolver, and a recovery device 18, for recovering monomer components and methanol vapor exiting the rectifier.

In practice polyethylene terephthalate (20) in a suitable form and size is introduced into the dissolver by any suitable means where it is liquified and reduced in chain length. The dissolver can be run at atmospheric pressure. Thus, simple solids handling devices such as rotary air locks can be employed to introduce the polyester resin. Suitable means for introducing the polyester include an air conveyor, a screw feeder, an extruder, and the like.

The dissolver is equipped with means for heating its contents to a temperature of up to about 305° C. In practice the dissolver is maintained at a temperature in the range of 240° to 260° C.

Reactor melt (22) and rectifier liquid (24) are introduced into the dissolver via suitable piping. Valves can be placed in their flow path to control the rate of introduction of these materials and their relative proportions. The reactor and rectifier are run at a higher pressure than the dissolver, thus eliminating the need for pumping means to transfer reactor melt and rectifier liquid to the dissolver, although pumping means can be employed, if desired.

Reactor melt and rectifier liquid introduced into the dissolver react with the polyester to shorten the average chain length. This initiates the depolymerization reaction and decreases the viscosity of the dissolver contents. In addition, there can be added to the dissolver an ester exchange catalyst, such as zinc acetate. Such catalysts are known in the art to facilitate the depolymerization process. The catalyst can be employed in a range of 0 to 800 parts by weight per million parts by weight of solid polyester introduced into the dissolver (ppm polyester). Preferably the catalyst is employed in the range of 30 to 300 ppm polyester, and most preferably the catalyst is employed in the range of 30 to 100 ppm polyester.

In a preferred embodiment, the melt in the dissolver is protected from the atmosphere by a blanket of nitrogen. This reduces degradation of the dissolver melt due to oxidation reactions.

The reactor melt and dissolver melt comprise methanol, low molecular weight polyesters, monomers, monohydric alcohol-ended oligomers, glycols, and dimethylterephthalate and methylhydroxyethyl terephthalate.

The major difference between these two melts is the average chain length of the polyester. The rectifier liquid contains the same components except for polyesters.

As indicated above, the viscosity of the dissolver melt is maintained in the range of 0.002 to 0.1 Pa.s. This is sufficiently low to permit the use of inexpensive pumping and heating means, and permits the reactor to be operated at optimum pressures to provide good yields of monomer. The flow rates of material in and out of the dissolver can be adjusted to maintain the viscosity at the desired level.

The dissolver also can be equipped with means for removing contaminants that are introduced with the polyester. Most contaminants are removed from the melt in the dissolver before introduction of the dissolver melt to reactor. Inorganic contaminants such as metals or sand are removed by a filter. Polyolefins and other contaminants that float on top of the dissolver melt are drawn off.

The gases (26) which evolve in the dissolver contain monomers that preferably are recovered together with the monomers exiting the reactor. This can be accomplished by passing the gases to the scrubber where they are treated with and absorbed by liquid methanol (28). This material (30) is then passed to the recovery device where it is combined with material (32) exiting the rectifier for recovery of the monomers.

Melt (34) from the dissolver is transferred to the reactor by suitable piping and pumps. If desired, a portion of the melt can be recirculated to the top of the dissolver to aid in the submersion of solid polyester being introduced into the dissolver. Alternatively or additionally, the reactor melt can be introduced into the dissolver to aid in the submersion of solid polyester.

Super-heated methanol vapor (36) can be provided to the reactor by conventional means. A preferred means is described in U.S. Pat. No. 5,051,528 to supply the methanol to the reactor and recover the methanol for reuse. The methanol introduced into the reactor heats the reactor contents and acts as a depolymerization agent. The effectiveness of the super-heated methanol for heating the reactor contents and for stripping gases depends on its volumetric flow rate; the depolymerization rate in the reactor therefore is a function of the methanol flow rate to the reactor. Methanol is introduced into the reactor at a rate in the range of 2 to 6 parts by weight methanol per part polyester.

There is transferred from the reactor to the rectifier a vapor stream (38) comprising methanol, dimethylterephthalate, glycols including ethylene glycol, diethylene glycol, and triethylene glycol, dimethylisophthalate, cyclohexanedimethanol, and methylhydroxyethyl terephthalate. The rectifier separates methylhydroxyethyl terephthalate from the vapor stream exiting the reactor and returns it to the dissolver in the form of a liquid (40) together with dimethyl terephthalate, glycols and methanol. Excess liquid (42) from the rectifier drains back into the reactor.

The remainder of the vapor stream (44) is transferred from the rectifier to recovery apparatus, where methanol (46) can be recovered for further use, and the glycol components (48) separated from the terephthalate components (50).

The invention has been described by reference to preferred embodiments, but it will be understood changes can be made to the apparatus and process steps specifically described herein within the spirit and scope of the invention.

What is claimed is:

1. A process for depolymerizing polyester into its components and separating the components using apparatus comprising:
   a dissolver for receiving polyester,
   a reactor for depolymerizing polyester into components, and
   a rectifier for separating polyester components; the process comprising the steps of:
   a) adding polyester to the dissolver and combining it with melt from the reactor and liquid from the rectifier to reduce the chain length of the polyester,
   b) transferring reduced chain length polyester from the dissolver to the reactor,
   c) passing super-heated methanol through the reactor to depolymerize polyester into its constituent monomers;
   d) transferring depolymerization products from the reactor to the rectifier; and
   e) separating the depolymerization products in the rectifier into a vapor phase containing component monomers and a liquid phase containing higher molecular weight materials;
   wherein
   i) the dissolver is operated at a temperature of 180° to 270° C. and a pressure of 80 to 150 kPaa,
   ii) the reactor is operated at a temperature in the range of 180° to 305° C., and a pressure in the range of 101 to 800 kPaa,
   iii) the relative proportions, on a weight basis, of melt from the reactor and liquid from the rectifier fed to the dissolver is in the range of 0 to 1 parts rectifier liquid per part reactor melt, and
   iv) the relative proportions, on a weight basis, of reactor melt plus rectifier liquid and polyester fed to the dissolver is in the range of 0 to 10 parts reactor melt plus rectifier liquid per part polyester, so that the viscosity of the polyester exiting the dissolver is maintained in the range of 0.001 to 0.2 Pa.s.

2. A process of claim 1, wherein the polyester resin is polyethylene terephthalate.

3. A process of claim 1, wherein the melt transferred from the reactor to the dissolver is comprised of depolymerization products and methanol.

4. A process of claim 1, where in the liquid transferred from the rectifier to the dissolver is comprised of methylhydroxyethyl terephthalate, dimethylterephthalate and methanol.

5. A process of claim 1, wherein:
   the dissolver is operated at a temperature in the range of 215° to 260° C. and a pressure in the range of 90 to 130 kPaa,
   the reactor is operated at a temperature in the range of 220° to 285° C., and a pressure in the range of 200 to 620 kPaa,
   the relative proportions, on a weight basis, of melt from the reactor and liquid from the rectifier fed to the dissolver is in the range of 0 to 0.5 parts liquid per part melt,
   the relative proportions on a weight basis of reactor melt plus rectifier liquid and polyester fed to the dissolver is in the range of 0.2 to 1 parts reactor melt plus rectifier liquid per part polyester, and the viscosity of the polyester exiting the dissolver is maintained in the range of 0.002 to 0.1 Pa.s.

6. A process of claim 1, wherein:
   the dissolver is operated at a temperature in the range of 240° to 255° C. and a pressure in the range of 95 to 105 kPaa,
   the reactor is operated at a temperature in the range of 250° to 280° C., and a pressure in the range of 240 to 410 kPaa,
   the relative proportions, on a weight basis, of melt from the reactor and liquid from the rectifier fed to the dissolver is in the range of 0 to 0.25 parts liquid per part melt,
   the relative proportions on a weight basis of reactor melt plus rectifier liquid and polyester fed to the dissolver is in the range of 0.2 to 0.4 parts reactor melt plus rectifier liquid per part polyester, and the viscosity of the polyester exiting the dissolver is maintained in the range of 0.01 to 0.04 Pa.s.

7. A process of claim 1, wherein the apparatus further comprises a scrubber for recovering gases exiting the dissolver.

8. A process of claim 1, wherein there is added to the dissolver an ester exchange catalyst in the amount of 1 to 800 ppm polyester.

9. A process of claim 1 wherein the average residence time of the polyester is in the range of 10 to 90 minutes.

10. A process of claim 5 wherein the ratio of rectifier liquid to reactor melt is in the range of 0.01 to 0.5 parts by weight.

* * * * *